United States Patent [19]

Ito

[11] 4,182,678
[45] Jan. 8, 1980

[54] MICRO-SCALE COUNTERCURRENT CHROMATOGRAPH

[75] Inventor: Yoichiro Ito, Bethesda, Md.

[73] Assignee: The United States of America as represented by the Secretary of the Department of Health, Education & Welfare, Washington, D.C.

[21] Appl. No.: 969,570

[22] Filed: Dec. 14, 1978

[51] Int. Cl.² .................................................. B01D 15/08
[52] U.S. Cl. ................................. 210/198 C; 55/197; 55/386
[58] Field of Search ............. 210/198 C, 31 C; 55/17, 55/67, 197, 386

[56] References Cited

U.S. PATENT DOCUMENTS

| 3,666,105 | 5/1972 | Fox, Jr. ........................... 210/198 C |
| 3,775,309 | 11/1973 | Ito et al. ......................... 210/198 C |
| 3,856,669 | 12/1974 | Ito et al. ......................... 210/198 C |
| 4,058,460 | 11/1977 | Ito ................................... 210/198 C |

*Primary Examiner*—John Adee
*Attorney, Agent, or Firm*—Browdy and Neimark

[57] ABSTRACT

A flow-through coil planet centrifuge having a hollow-walled, vertical-axis rotating bowl with a helically-coiled long separation column spirally contained in the hollow wall of the bowl. A stationary, vertical-axis drive motor is located in axial alignment with the bowl. The bowl is rotatably coaxially supported in a cage-like frame. The bowl is rotated by the motor via the frame by a system of belts and gearing which compensates for the rotation of the bowl and column relative to the motor and frame to avoid the twisting of the flow tubes of the column. The outer portion of the frame is provided with a vertical support tube for the flow tubes to prevent excessive strain on the tubes during high speed revolution of the frame.

13 Claims, 11 Drawing Figures

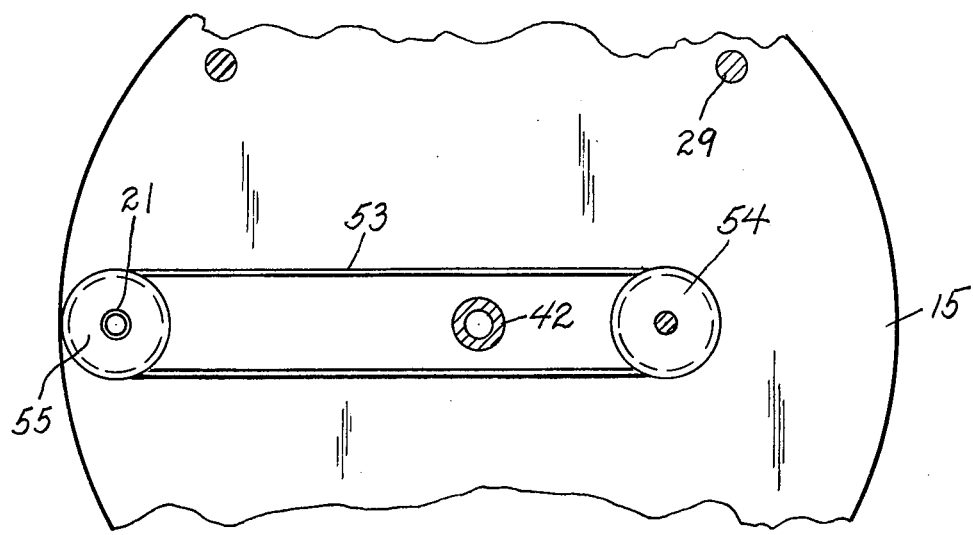
FIG.4
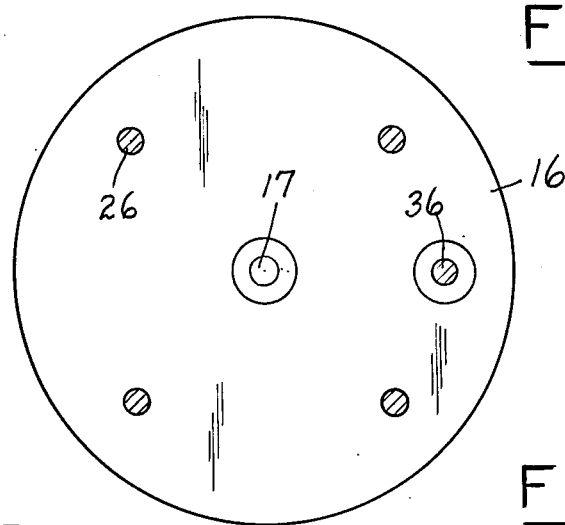
FIG.5
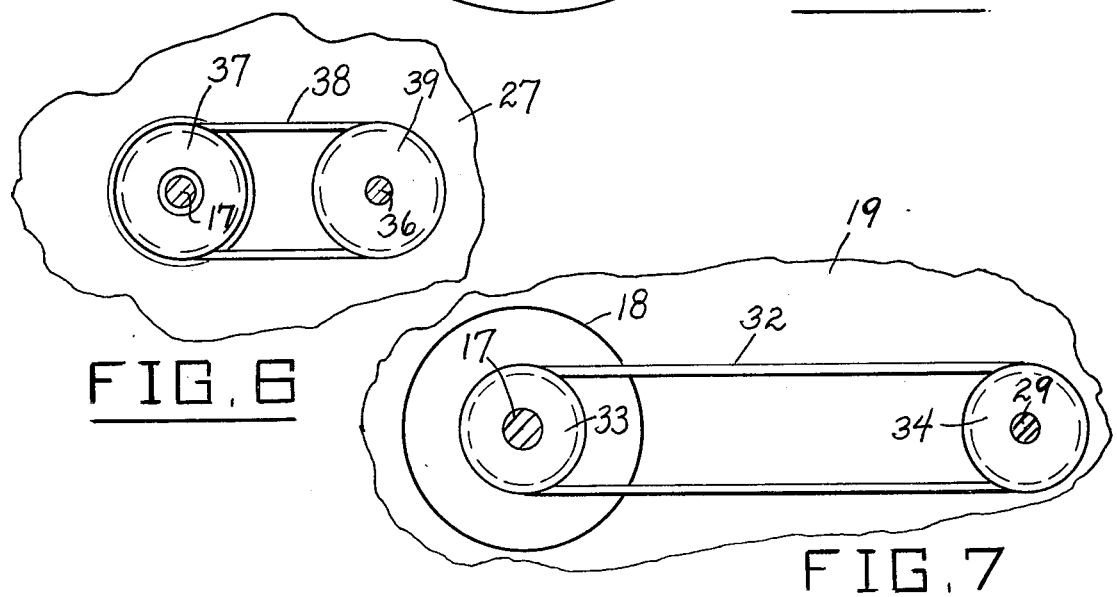
FIG.6
FIG.7

MICRO-SCALE COUNTERCURRENT CHROMATOGRAPH

FIELD OF THE INVENTION

This invention relates to centrifugal liquid processing apparatus, and more particularly to a coil planet centrifuge apparatus of the flow-through vertical-axis type employing a helically-coiled countercurrent separation column.

BACKGROUND OF THE INVENTION

Various methods of countercurrent chromatography have been proposed, for example, methods as disclosed in the article by Ito and Bowman in "Journal of Chromatographic Science", Vol. 8, pp 315-323, June 1970. These methods include helix countercurrent chromatography, droplet countercurrent chromatography, and rotational and gyratory-movement countercurrent chromatography.

The theoretical considerations involved in helix countercurrent chromatography have been pointed out in detail in U.S. Pat. No. 3,775,309, to Ito and Bowman, and in an article by Ito, et al., in "Analytical Chemistry", Vol 41, pp. 1579-1584, October 1969, cited in said U.S. patent. It was noted in said patent that flow became difficult because of the need for rotating seals, and because of this, flow-through operation was somewhat impractical and that the practical use of the method was limited by problems of sample introduction and fractionation.

A preliminary search of the prior art revealed the following prior U.S. patents, which appear to indicate the present state of the art:

Ito, U.S. Pat. No. 3,775,309
Ito, U.S. Pat. No. 3,856,669
Khoja, et al., U.S. Pat. No. 3,986,442

SUMMARY OF THE INVENTION

The present invention overcomes the problems of previously proposed flow-through centrifuge devices employed for micro-scale countercurrent chromatography. It employs a separation column in the form of a coiled tube which is again coiled around the periphery of a centrifuge bowl. When the coiled tube is first filled with one phase (stationary phase) of an equilibrated two-phase solvent system and the other phase (mobile phase) is introduced at one end of the coiled tube, rotation of the column produces a centrifugal force field which retains a substantial amount of the stationary phase in each coil unit while the mobile phase continuously percolates through the stationary phase segment. Consequently, solutes locally introduced at the entrance of the coiled tube are subjected to an efficient partition process between the two phases in each coil unit and are eluted out in the order of their relative partition coefficients. The efficiency of separation in this technique can be increased by using a fine long tube coiled onto a small core. Thus, achievement of high efficiency of separations can be attained by the use of a relatively long cylindrical centrifuge bowl to accommodate such a long coiled column, together with the use of a high revolutional speed to overcome the plug flow of the two-phase segments which would otherwise take place in a narrow space in the coiled tube. These requirements are fulfilled by the present invention, which provides an extremely stable centrifuge system and which has greatly improved structure for stabilizing the system under high centrifugal force field conditions.

Accordingly, a main object of the present invention is to provide an improved flow-through centrifuge device which overcomes the deficiencies and disadvantages of previous devices employed for countercurrent chromatography.

A further object of the invention is to provide an improved flow-through centrifuge device for micro-scale countercurrent chromatography which does not employ rotating seals, which has continuous flow-through capability, which is highly efficient and which will permit separation of very small quantities of solutes without much dilution.

A still further object of the invention is to provide an improved flow-through centrifuge device which can operate under a high centrifugal force field with extreme stability, which has a coil-carrying bowl rotatably supported at both top and bottom so as to minimize instability of the system at high revolutional speeds, which is dynamically balanced, which employs simple and efficient intercoupling means to avoid the need for rotating seals and to prevent twisting of its flow tubes, and which includes supporting and guide means for supporting a large portion of the flow tubes at the location where the acting centrifugal force is a maximum, whereby the flow tubes suffer minimum strain during high speed revolution.

BRIEF DESCRIPTION OF THE DRAWINGS

Further objects and advantages of the invention will become apparent from the following description and claims, and from the accompanying drawings, wherein:

FIG. 4 is a fragmentary horizontal cross-sectional view taken substantially on line 4—4 of FIG. 1.

FIG. 5 is a horizontal cross-sectional view taken substantially on line 5—5 of FIG. 1.

FIG. 6 is a horizontal cross-sectional view taken substantially on line 6—6 of FIG. 1.

FIG. 7 is a horizontal cross-sectional view taken substantially on line 7—7 of FIG. 1.

DESCRIPTION OF A PREFERRED EMBODIMENT

Figure 1:
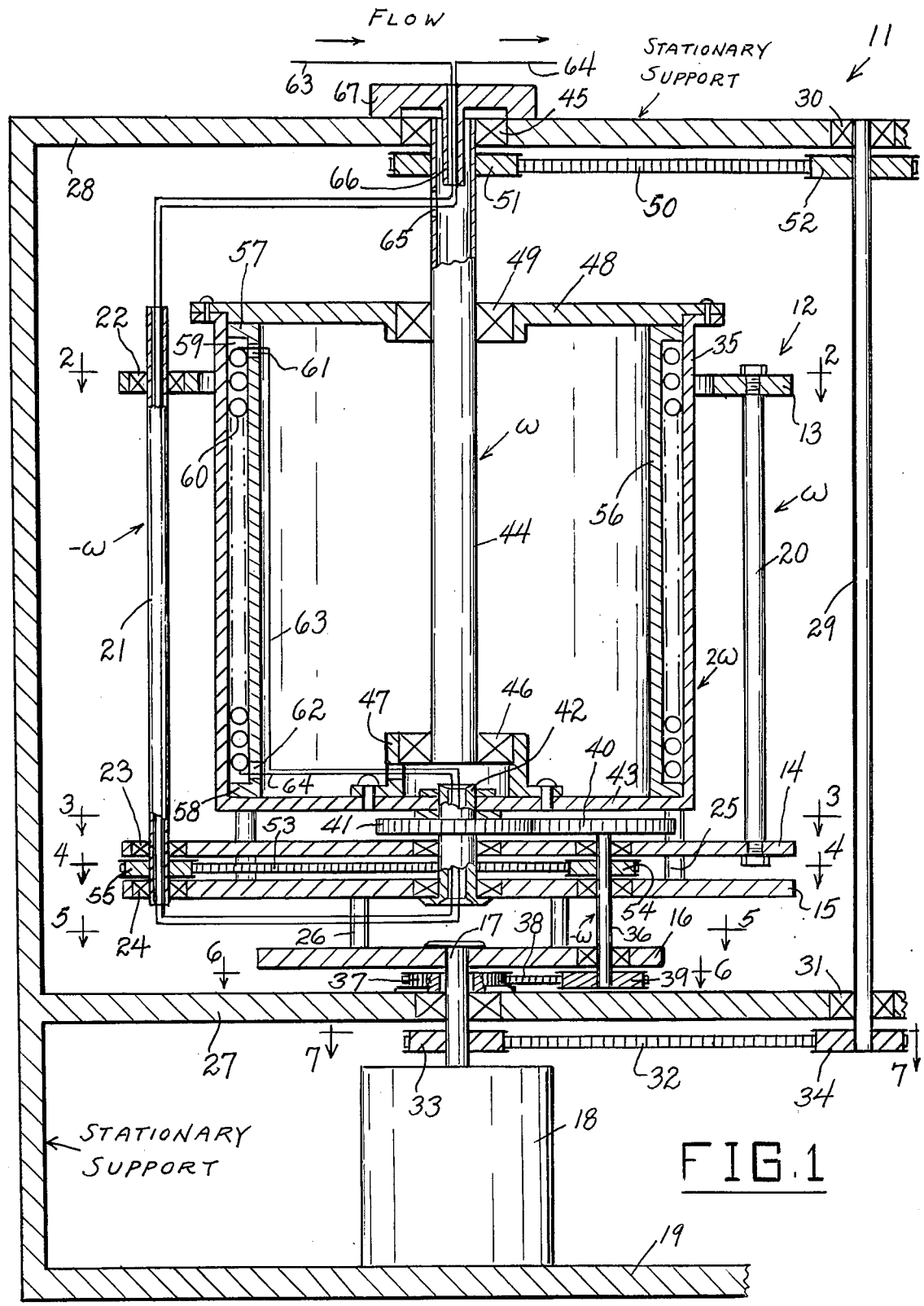
FIG. 1 is a vertical cross-sectional view taken through an improved flow-through micro-scale countercurrent centrifuge device constructed in accordance with the present invention.
Figure 2:
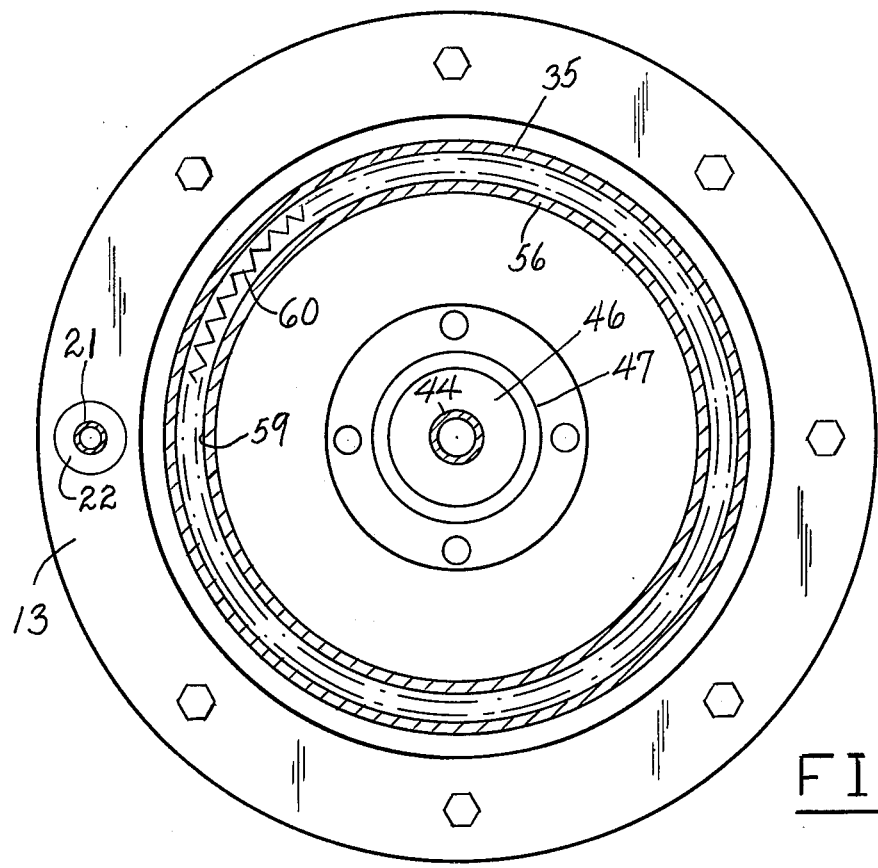
FIG. 2 is a horizontal cross-sectional view taken substantially on line 2—2 of FIG. 1.
Figure 3:
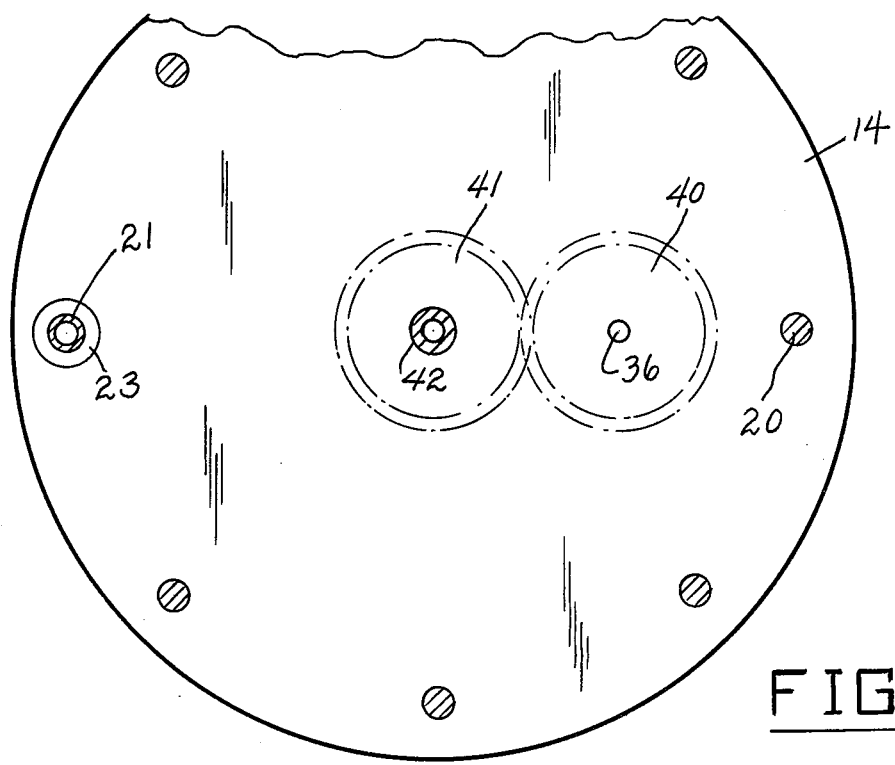
FIG. 3 is a fragmentary horizontal cross-sectional view taken substantially on line 3—3 of FIG. 1.

Referring to the drawings, 11 generally designates a flow-through centrifuge device according to the present invention. The device 11 comprises a cage-like rotor assembly 12 formed by a flat top ring 13 and three vertically spaced bottom circular plate members 14, 15 and 16 rigidly linked together coaxially and driven, in a manner presently to be described, by the vertical shaft 17 of an electric motor 18 mounted on a stationary base member 19 coaxially with members 14, 15 and 16. The top ring 13 is rigidly connected to plate member 14 by a plurality of spaced vertical tie bars 20, and a vertical tubular long guide shaft 21 is supportingly journalled by bearings 22, 23 and 24 in the respective members 13, 14 and 15, as shown in FIG. 1. The spaced parallel circular plate members 14, 15 are rigidly connected by a plurality of spaced short vertical rod elements 25, and the lower, smaller-diameter circular plate member 16 is rigidly connected to plate member 15 by a plurality of spaced vertical rod elements 26.

Motor shaft 17 is rigidly connected at its top end to the center of lower circular plate member 16 and extends through and is journalled in a horizontal bottom stationary support plate 27. Spaced above the cage-like rotor 12 is a horizontal top stationary support plate 28.

Spaced laterally from the rotor assembly 12 is a vertical shaft 29 which is supportingly journalled by respective bearings 30, 31 in upper support plate 28 and lower support plate 27. Motor 18 is drivingly coupled to shaft 29 by a toothed belt 32 drivingly engaging around respective identical toothed pulleys 33 and 34 secured on motor shaft 17 and on the bottom end of shaft 29.

The cage-like rotor frame 12 holds three rotary structures, namely, a centrifugal bowl 35, a vertical countershaft 36 and the above-described vertical long hollow shaft 21. A stationary annular toothed pulley 37 is rigidly secured on support plate 27 coaxially around motor shaft 17 and is drivingly coupled by a toothed belt 38 to an identical toothed pulley 39 secured on the bottom end of shaft 36.

Shaft 36 extends through and is supportingly journalled in the spaced circular plate members 14, 15 and 16 by suitable bearings. Secured on the top end of shaft 36 is a gear 40 which meshes with an identical gear 41 rigidly secured on a vertical tubular bowl-supporting shaft 42 supportingly journalled by suitable bearings centrally in circular plate members 14, 15. The top end of shaft 42 extends through and is rigidly supportingly secured to the center of the bottom circular wall 43 of bowl 35.

To further stabilize the system, the central bowl 35 is also supported by a central tubular shaft 44 supportingly journalled at its top end in the upper stationary horizontal plate member 28 by a supporting bearing assembly 45. The bottom end of tubular shaft 44 is coaxially supportingly connected to the bowl bottom wall 43 by a supporting bearing assembly 46 mounted in an annular bushing member 47 coaxially secured to said bottom wall. Shaft 44 extends through and is journalled in the circular top cover 48 of bowl 35 by a suitable bearing assembly 49. Thus, the central bowl 35 is rotatably supported from the top and at the bottom, which makes it possible to minimize any instability of the system at high revolutional speeds.

Central shaft 44 is drivingly coupled to side shaft 29 by a toothed drive belt 50 drivingly engaged around respective identical toothed pulleys 51 and 52 secured on shafts 44 and 29.

Countershaft 36 is drivingly coupled to tubular guide shaft 21 by a toothed drive belt 53 drivingly engaged around respective toothed pulleys 54 and 55 secured on countershaft 36 and tubular shaft 21.

The bowl 35 has a hollow peripheral wall, defined by an inner liner sleeve 56 with top and bottom annular flanges 57 and 58. The sleeve 56 is engaged snugly in and suitably secured in the main cylindrical outer shell of the bowl to define an annular space 59. The coiled separation tube, shown at 60, is helically coiled around the bowl in the annular space 59 to define a long coiled helical column. The column may be formed by employing a fine long tube coiled onto a small core, to increase the efficiency of separation, as above mentioned. The sleeve 56 is provided with top and bottom apertures 61, 62 for the inlet and outlet flow tubes 63, 64 of the separation column.

As shown in FIG. 1, the flow tubes 63, 64 are led downwardly through the central tubular shaft 42, then laterally, and then upwardly through the long hollow shaft 21. From the top end of shaft 21 the flow tubes extend through an aperture 65 in hollow shaft 44 and thence upwardly through a stationary supporting tube 66 depending axially from a bushing member 67 secured to the top stationary plate member 28 over bearing 45.

As will be presently explained, the central shaft 44 rotates synchronously with the rotor assembly 12, so that the side hole 65 always faces vertical hollow shaft 21, whereby friction can be avoided between the flow tubes and the central shaft 44 provided that said side hole is sufficiently large in size.

Because the long hollow shaft 21 can support a large portion of the flow tubes at the location where the acting centrifugal force is greatest, the flow tubes suffer minimum strain during a high-speed revolution.

In operation, when the motor 18 drives the rotor assembly 12 at an angular velocity $\omega$, the countershaft 36 on said assembly rotates at an angular velocity of $-\omega$ around its own axis. This motion is conveyed to the central bowl 35 via the 1:1 gear coupling provided between the countershaft 36 and the central bowl 35 by the meshing identical gears 40, 41. Thus, the central bowl 35 rotates at an angular velocity of $2\omega$ in the same direction as the rotor assembly 12 with respect to a stationary observer, or at an angular velocity of $\omega$ with respect to the rotor assembly 35. Due to the driving coupling of countershaft 36 to hollow shaft 21 provided by belt 53 and toothed pulleys 54, 55, the hollow shaft 21 rotates at an angular velocity of $-\omega$ about its own axis on the rotor assembly 12. The long hollow shaft 21 is stably supported by the ring 13 forming the rigid top of the rotor assembly 12. This ring also provides efficient dynamic balancing by allowing the use of the counterbalancing weight afforded by the diametrically opposite tie rod 20. As above mentioned, the system is further stabilized by the top support for the bowl provided by depending hollow central rotary shaft 44. This central shaft 44 is rotated at an angular velocity $\omega$, the same angular velocity as the rotor assembly 12, by means of the 1:1 ratio coupling provided by belt 50 and toothed pulleys 51, 52 mounted respectively on shaft 44 and side shaft 29.

Thus, although the flow tubes 63, 64 may reversibly torsionally flex to some extent in tubes 66 and 42 during operation of the apparatus, said flow tubes will be prevented from twisting.

It has been demonstrated that the apparatus will operate successfully with a separation column having a bore of 0.4 mm inside diameter. The apparatus will permit the use of a separation column with an inside diameter as small as 0.1 mm, thereby allowing the separation of picogram quantities of solutes without much dilution.

Figure 8:
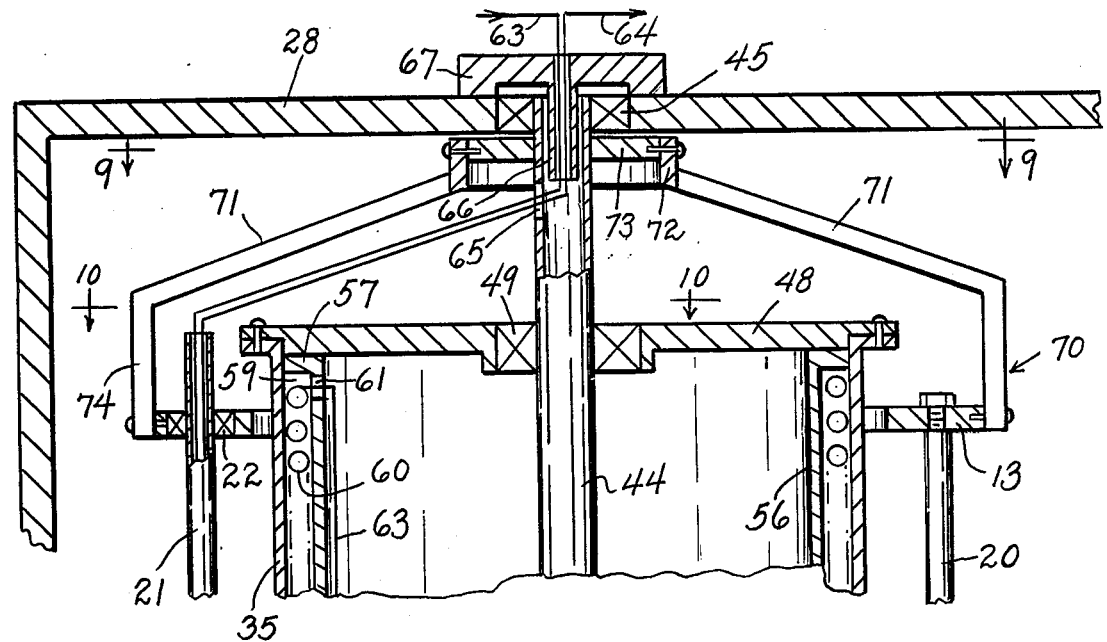
FIG. 8 is a fragmentary vertical cross-sectional view showing the upper portion of a modified form of countercurrent centrifuge device according to the present invention.
Figure 9:
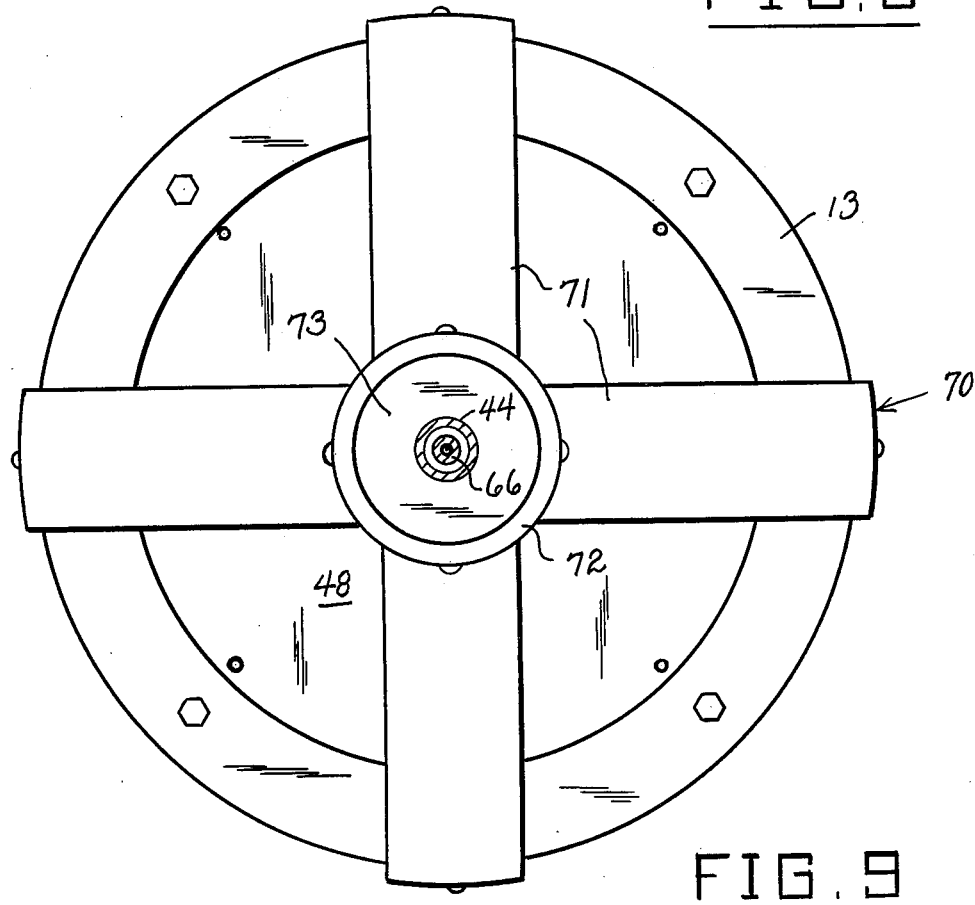
FIG. 9 is a horizontal cross-sectional view taken substantially on line 9—9 of FIG. 8.
Figure 10:
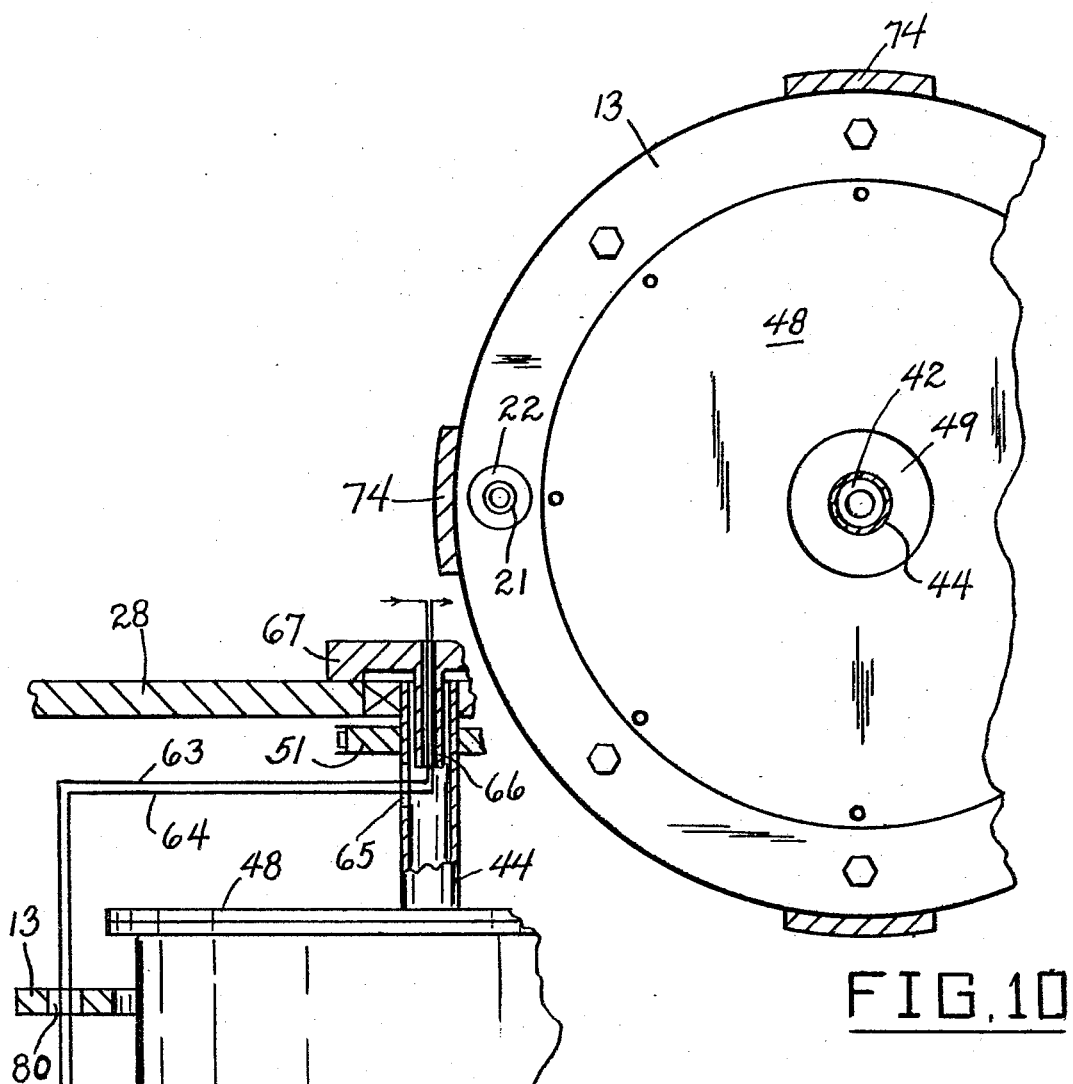
FIG. 10 is a horizontal cross-sectional view taken substantially on line 10—10 of FIG. 8.

In the modification shown in FIGS. 8 to 10, the side shaft 29 of the apparatus of FIG. 1 is eliminated, and the central shaft 44 is directly connected to the ring 13 by a multiple-arm spider-like bridge assembly 70 having a plurality of uniformly spaced radially extending connection arms 71. The arms 71 extend downwardly and outwardly from a central collar 72 which surrounds and is rigidly secured to a disc member 73, which in turn is rigidly secured to the upper portion of hollow shaft 44 subjacent to the bearing assembly 45. The outer ends of the arms 71 have depending vertical portions 74 which are rigidly secured to the outer periphery of ring member 13. The direct connection provided by the bridge assembly 70 provides substantially the same function as the side shaft 29 and the driving toothed pulley and belt couplings associated therewith, employed in the embodiment of FIG. 1.

Figure 11:
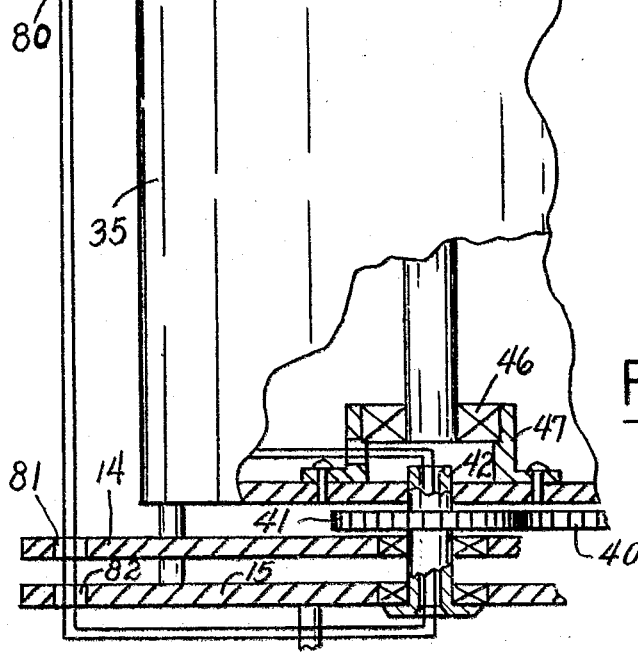
FIG. 11 is a fragmentary vertical cross-sectional view showing another modification of the present invention.

When the centrifugal acceleration field is moderate, or if the flow tubes are of a disposable type, intended for a short period of use, after which they are replaced, the use of the hollow supporting guide shaft 21 and its counter-rotating drive mechanism can be omitted and the flow tubes 63,64 can be simply passed through suitable holes 80, 81 and 82 provided in ring member 13 and the top and middle plate members 14 and 15 of the rotor assembly 12, in the manner illustrated in FIG. 11.

While certain specific embodiments of an improved flow-through coil planet centrifuge apparatus have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A flow-through coil planet centrifuge apparatus comprising stationary support means, stationary drive motor means having a vertical output shaft, a rotor frame coaxially drivingly mounted on said vertical output shaft, a bowl member coaxially positioned in said rotor frame and having a tubular bottom axial shaft, means supportingly rotatably axially connecting said bottom axial shaft to said rotor frame, vertical depending hollow shaft means journalled in said stationary support means above the bowl member, means axially rotatably and supportingly connecting said depending shaft means to said bowl member, a coiled separation column coaxially mounted on and coiled around the periphery of said bowl member, said column having inlet and outlet flow tubes extending downwardly through said tubular bottom axial shaft and upwardly through said depending hollow shaft means, planet gearing means drivingly intercoupling said tubular bottom axial shaft, rotor frame and stationary support means to drive said bowl member responsive to rotation of said rotor frame, and means drivingly intercoupling said vertical output shaft and depending hollow shaft means so as to avoid twisting of said flow tubes during rotation of said bowl member relative to said stationary support means.

2. The coil planet centrifuge apparatus of claim 1, and wherein said bowl member has a hollow peripheral wall, and wherein said coiled separation column is contained in said hollow peripheral wall.

3. The coil planet centrifuge apparatus of claim 1, and wherein said rotor frame is provided with a vertical rotary outer guide tube receiving said flow tubes, and means to rotate said guide tube oppositely relative to said rotor frame substantially at the same speed of rotation as the rotor frame rotates relative to said stationary support means.

4. The coil planet centrifuge apparatus of claim 3, and wherein said rotor frame includes a horizontal top ring member and a lower plate assembly rigidly connected to the top ring member, and wherein said rotary outer guide tube is journalled between said top ring member and lower plate assembly.

5. The coil planet centrifuge apparatus of claim 4, and wherein said lower plate assembly comprises a plurality of vertically spaced coaxial circular plate members and means rigidly interconnecting said coaxial circular plate members.

6. The coil planet centrifuge apparatus of claim 1, and wherein said bowl member has a top cover and said depending hollow shaft means extends rotatably and supportingly through said top cover and is rotatably and supportingly connected to the center portion of the bottom of the bowl member.

7. The coil planet centrifuge apparatus of claim 1, and wherein said rotor frame includes a horizontal top ring member and a lower plate assembly, a plurality of spaced vertical tie bars rigidly connecting the ring member to said lower plate assembly, a vertical rotary guide tube journalled in said ring member and lower plate assembly diametrically opposite one of the tie bars and supportingly receiving said flow tubes, and means to rotate said guide tube oppositely relative to said rotor frame at substantially the same speed of rotation as the rotor frame rotates relative to said stationary support means.

8. The coil planet centrifuge apparatus of claim 1, and wherein said planet gearing means comprises a stationary gear mounted on the stationary support means coaxially with said tubular bottom axial shaft, a vertical countershaft journalled on the rotor frame, means gearingly coupling said stationary gear to said countershaft, and gear means intercoupling said countershaft and said tubular bottom axial shaft.

9. The coil planet centrifuge apparatus of claim 8, and wherein said rotor frame includes a horizontal top ring member and a lower plate assembly, means rigidly connecting said ring member to said lower plate assembly, a vertical guide tube journalled in said ring member and supportingly receiving said flow tubes, and means gearingly coupling said guide tube to said countershaft to rotate said guide tube oppositely relative to said rotor frame at substantially the same speed of rotation as the frame rotates relative to said stationary support means.

10. The coil planet centrifuge apparatus of claim 9, and wherein said means rigidly connecting the ring member to said lower plate assembly comprises a plurality of spaced vertical tie bars rigidly connected between the ring member and lower plate assembly, one of the tie bars being located diametrically opposite said vertical guide tube.

11. The coil planet centrifuge apparatus of claim 1, and wherein said means drivingly intercoupling said vertical output shaft and depending hollow shaft means comprises means rigidly connecting said depending hollow shaft means to said rotor frame.

12. The coil planet centrifuge apparatus of claim 1, and wherein said means drivingly intercoupling said vertical output shaft and depending hollow shaft means comprises a horizontal top ring member coaxially mounted on said rotor frame and a bridge assembly rigidly connecting said ring member to said hollow shaft.

13. The coil planet centrifuge apparatus of claim 12, and wherein said bridge assembly comprises a plurality of radially outwardly extending arms rigidly secured to said hollow shaft means and means rigidly connecting the outer ends of said arms to said ring member.

* * * * *